US00PP08590P

United States Patent [19]

Warriner, deceased

[11] Patent Number: Plant 8,590

[45] Date of Patent: Feb. 15, 1994

[54] HYBRID TEA ROSE PLANT NAMED 'JACBUTE'

[75] Inventor: William A. Warriner, deceased, late of Tustin, Calif., by Alene B. Warriner legal representative

[73] Assignee: Bear Creek Gardens, Inc., Medford, Oreg.

[21] Appl. No.: 883,191

[22] Filed: May 14, 1992

[51] Int. Cl.[5] ..... A01H 5/00

[52] U.S. Cl. ..... Plt./11

[58] Field of Search ..... Plt. 11, 22, 18, 19, Plt. 26, 27

*Primary Examiner*—Howard J. Locker

*Attorney, Agent, or Firm*—Klarquist, Sparkman, Campbell, Leigh and Whinston

[57] ABSTRACT

A hybrid tea rose created by crossing the variety JACmas, U.S. Plant Pat. No. 2,998, with the variety JACrose, U.S. Plant Pat. No. 4,850, is characterized by its strong, pleasant fragrance, its unusual and distinctive red and yellow-orange flower color, its resistance to powdery mildew and rust, its many flowers, and the presence of glands on the stipules, sepals and peduncles and many small prickles on the rachis underside.

1 Drawing Sheet

The present invention relates to a new and distinct variety of rose plant of the hybrid tea class which was originated by me by crossing the variety JACmas, U.S. Plant Pat. No. 2,998, with the variety JACrose, U.S. Plant Pat. No. 4,850.

The primary objective of this breeding was to produce a new rose variety having the large flower and fragrance of JACmas combined with the abundant flowers of the variety JACrose. The objective was substantially achieved along with other desirable improvements as evidenced by the following unique combination of characteristics which are outstanding in the new variety and which distinguish it from its parents, as well as from all other varieties of which I am aware:

1. Strong, pleasing fragrance;
2. Unusual flower color;
3. Presence of glands on stipules, sepals and peduncle;
4. Presence of many small hooked prickles on the rachis underside;
5. Resistance to powdery mildew and rust;
6. Production of many flowers.

Asexual reproduction of this new variety by budding, as performed at Wasco and Somis, Calif., shows that the foregoing characteristics and distinctions come true to form and are established and transmitted through succeeding propagations.

The accompanying photograph shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—JACmas, U.S. Plant Pat. No. 2,998.

*Pollen parent.*—JACrose, U.S. Plant Pat. No. 4,850.

Classification:

*Botanical.*—*Rosa hybrida.*

*Commercial.*—Hybrid tea.

FLOWER

Observations made from specimens grown in a garden environment in Somis, Calif., in May-August of 1991.

Blooming habit: Recurrent.

Bud:

*Size.*—1½ inches when the petals start to unfurl.

*Form.*—Long pointed ovoid.

*Color.*—When sepals first divide, bud color is Yellow-orange Group 22B with markings of Red Group 51B. When half blown, the upper sides of the outer petals are Red Group 54B on the petal edges; in the interior of the flower, the petals are Yellow Orange Group 22D. The lower sides of the petals are Yellow Orange Group 22D.

*Sepals.*—Color: Green Group 138C. Surface texture: Glandular. There are three normally appendaged sepals. There are two unappendaged sepals with hairy edges.

*Receptacle.*—Color: Green Group 143C. Shape: Funnel. Size: Medium, 5/16"×⅜". Surface: Smooth.

*Peduncle.*—Length: Medium, 2¼"–½". Surface: Glandular. Color: Light green. Strength: Stiff, erect.

Bloom:

*Size.*—Large. Average open size is 5 inches.

*Borne.*—Singly.

*Stems.*—Medium, strong, 14"–18".

*Form.*—When first open: High center. Permanence: Retains its form to the end, outer petals curl back, quill fashion.

*Petalage.*—Number of petals under normal conditions: 30–35.

*Color.*—The upper side of the petal is Red Group 54B on the outer petal edges with Yellow-Orange Group 22D in the interior of the flower. The reverse side of the petals is Red Group 54B on the outer edges with the rest of the reverse side Yellow-Orange 22C. The base of the petals has a bright yellow half moon ¼"×¼" at the point of attachment. The major color on the upper side is Yellow-Orange group 22D.

*Variegations.*—None.

*Discoloration.*—The general tonality at the end of the first day: Some increase in the Red Group 54B pigment. At the end of the third day, little change as the flower opens.

*Fragrance.*—Strong.

Petals:

*Texture.*—Thick.

*Shape.*—Round.

*Form.*—Moderately quilled.

*Arrangement.*—Imbricated, with no petaloids in the center.

*Persistence.*—Drop off cleanly.

*Lastingness.*—On the plant: Long, 5–7 days. As a cut flower: Long, 7–8 days.

Reproductive parts:

*Anthers.*—Size: Medium. Quantity: Many. Color: Yellow. Arrangement: Regular around styles.

*Filaments.*—Color: Yellow.

*Pollen.*—Color: Lemon-Yellow.

*Styles.*—Color: Red.

*Stigmas.*—Color: Greenish-white.

Form: Bush.

Growth: Very vigorous; upright, branching.

Folliage:

*Number of leaflets on normal mid-stem leaves.*—5 or 7.

*Size.*—Large, 6″×4″.

*Quantity.*—Normal.

*Color.*—New foliage: Dark reddish-bronze. Old foliage: Dark green.

Leaflets:

*Shape.*—Pointed oval.

*Texture.*—Upper side: Leathery, smooth.

*Edge.*—Serrated.

*Serration.*—Single, small.

*Petiole rachis.*—Color: Reddish.

*Petiole underside.*—Rough, with prickles.

*Stipules.*—Short, bearded with many glands.

*Disease resistance.*—Resistant to mildew and rust under normal growing conditions at Somis, Calif.

Wood:

*New wood.*—Color: Light green. Bark: Smooth.

*Old wood.*—Color: Green. Bark: Smooth.

Prickles:

*Quantity.*—On main canes from base: Ordinary. On laterals from main canes: Ordinary.

*Form.*—Hooked downward.

*Color when young.*—Red.

Small prickles:

*Quantity.*—On main stalks: None. On laterals: None.

I claim:

1. A new and distinct variety of rose plant of the hybrid tea class, substantially as herein shown and described, characterized particularly as to novelty by the unique combination of its strong pleasant fragrance, its unusual and distinctive flower color, the presence of glands on peduncles, stipules and sepals, the presence of many small prickles on the rachis underside and its resistance to powdery mildew and rust in Somis, Calif.

* * * * *

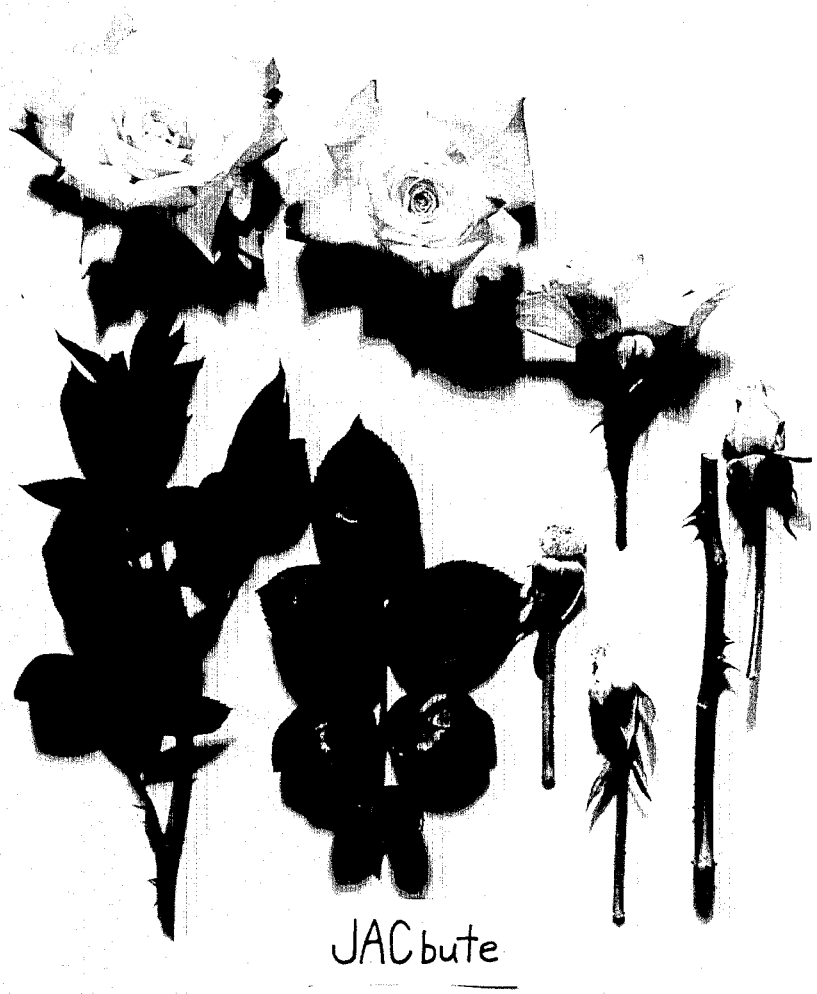
JACbute

UNITED STATES PATENT AND TRADEMARK OFFICE

CERTIFICATE OF CORRECTION

PATENT NO. : PP 8,590

DATED : February 15, 1994

INVENTOR(S) : William A. Warriner, Deceased

It is certified that error appears in the above-indentified patent and that said Letters Patent is hereby corrected as shown below:

Column 2, Line 25, "2 1/4" - 1/2"" should be --2 1/4" - 2 1/2"--.

Signed and Sealed this

Eighteenth Day of October, 1994

*Attest:*

*Attesting Officer*

BRUCE LEHMAN

*Commissioner of Patents and Trademarks*